United States Patent
Miyamoto

[11] Patent Number: 5,573,942
[45] Date of Patent: Nov. 12, 1996

[54] METHOD FOR ARRANGING CELLS IN A CULTURE MEDIUM

[75] Inventor: Shigeyuki Miyamoto, Tokyo, Japan

[73] Assignee: NEC Corporation, Tokyo, Japan

[21] Appl. No.: 435,788

[22] Filed: May 5, 1995

Related U.S. Application Data

[62] Division of Ser. No. 318,086, Oct. 5, 1994.

[30] Foreign Application Priority Data

Oct. 6, 1993 [JP] Japan .................. 5-250250

[51] Int. Cl.$^6$ .................................................. C12N 5/00
[52] U.S. Cl. .................................................. 435/240.243
[58] Field of Search .................. 435/240.21, 240.23, 435/240.243, 284.1, 299.1, 317.1

[56] References Cited

U.S. PATENT DOCUMENTS

| | | | |
|---|---|---|---|
| 4,339,537 | 7/1982 | Sogi | 435/240 |
| 5,202,227 | 4/1993 | Matsuda | 430/320 |
| 5,278,063 | 1/1994 | Hubbell | 435/240.243 |
| 5,330,911 | 7/1994 | Hubbell | 435/240.243 |
| 5,348,877 | 9/1994 | McKenna | 435/240.21 |
| 5,369,012 | 11/1994 | Koontz | 435/7.92 |
| 5,385,836 | 1/1995 | Kimura | 435/177 |
| 5,470,739 | 11/1995 | Akaike | 435/240.243 |
| 5,480,827 | 1/1996 | Guillemin | 435/240.23 |

FOREIGN PATENT DOCUMENTS

| | | |
|---|---|---|
| 2-245281 | 9/1990 | Japan . |
| 3-7576 | 1/1991 | Japan . |
| 3-7577 | 1/1991 | Japan . |
| 5-176753 | 7/1993 | Japan . |

*Primary Examiner*—Carolyn Paden
*Attorney, Agent, or Firm*—Sughrue, Mion, Zinn, Macpeak & Seas

[57] ABSTRACT

An apparatus for arranging cells in a culture medium includes a substrate having patterns on a surface thereof, the patterns each having different adhesive property to cells, a container containing therein the substrate, cells and liquid culture medium for incubating the cells, and a shaker for shaking, rotating or oscillating the container. The apparatus assures that cells stick only to a pattern on which a material to which cells are easy to stick is applied, and do not stick to a pattern on which the material is not applied.

2 Claims, 3 Drawing Sheets

METHOD FOR ARRANGING CELLS IN A CULTURE MEDIUM

This is a divisional of application Ser. No. 08/318,086 filed Oct. 5, 1994.

BACKGROUND OF THE INVENTION

1. Field of the Invention

The invention relates to an apparatus for arranging cells on a substrate in a pattern in a culture container, and also to a method for the same.

2. Description of the Related Art

Presently, cells of various animals or plants are cultivated, and new methods for cultivation are now being researched. Techniques of cultivation are utilized for analyzing biochemical phenomena and properties of cells and for generating a new, useful substance. In addition, attempts are now being made to analyze physiological activity or toxicity of artificially made medicines, using cultivated cells.

Particular cells, in particular most animal cells, have a property that they have to attach to something to grow, and hence they cannot live in a long term if they are in a floating condition in vitro. It is necessary to prepare a substrate to which cells attach for incubating such cells having the aforementioned property. In general, a culture dish made of plastic is used as a substrate, and protein (such as collagen and fibronectin) to which cells easily attach is uniformly applied thereto. It is known that the above mentioned protein acts on cells being cultivated to thereby make it easy for cells to attach to the protein and affect a shape of cells.

There has been suggested a technique for attaching cultivated cells only to a small portion of a substrate to thereby arrange cells on a desired region. This technique allows cultivated cells to be applied to an artificial organ, a biosensor and a bioreactor. For arranging cells on a desired region, a method in which a substrate having a plurality of patterns on a surface thereof has been used. Each of the patterns has different adhesive property to cells. Cells are introduced to attach only to the patterns which are processed so that cells are easy to attach thereto, to thereby arrange cells on a particular region in which the cells are to be incubated.

Japanese Unexamined Patent Public Disclosure No. 2-245181 has suggested the use of an electric charge carrying medium on which electrostatic charge patterns are formed for proliferating nerve cells in a circuit-like configuration. Japanese Unexamined Patent Public Disclosure No. 3-7576 attempts an arrangement of cultivated cells on a surface on which optically sensitive hydrophilic high polymers, which includes high polymers to which cells can attach and high polymers to which cells cannot attach, are patterned by a photolithography process. Japanese Unexamined Patent Public Disclosure No.3-7577 suggests the use of functional groups to which cells can attach, formed by radiating ultraviolet rays and/or radioactive rays to cell incubating material having a surface to which cells cannot attach, and also suggests the use of polymerization initiator species formed by radiating ultraviolet rays and/or radioactive rays to cell incubating material. On the functional groups or the polymerization initiator species are polymerized monomer, which includes monomer to which cells can attach and monomer to which cells cannot attach, to form patterns on a surface to thereby control arranging cells.

Japanese Unexamined Patent Public Disclosure No. 5-176753 discloses the use of a cell incubating substrate on which is patterned a material such as collagen influencing cell shape and degree of cell attachment, and also discloses a method for fabricating such a substrate by means of a photolithography process. By incubating cells on such a substrate, it is possible to attach cells to an area on which collagen is patterned to thereby accomplish patterning of cells.

In conventional methods for arranging cultivated cells in a desired pattern, a culture container containing therein cells and culture medium is allowed to stand when cells are incubated, similar to conventional methods for cultivating cells. However, in conventional methods in which a culture container is allowed to stand while incubating cells, when cells stay on an area which is processed so that cells should not attach thereto, the cells secrete extracellular matrix and thus may undesirably attach to the area anyway. As a result, cells can attach to an area on which cells are not desired and to thereby pose a problem that a resolution of cell arrangement is deteriorated.

SUMMARY OF THE INVENTION

In view of the foregoing problem, it is an object of the present invention to provide an apparatus and a method for arranging cells on a desired area in a culture container to thereby provide a higher resolution of cell arrangements.

In one aspect, the invention provides an apparatus for arranging cells in a culture medium including a substrate having patterns on a surface thereof, the patterns each having different adhesive property to cells, a container containing therein the substrate, cells and liquid culture medium for incubating the cells, and a device for rotating or oscillating the container.

In a preferred embodiment, the device for rotating or oscillating the container is a shaker.

In another preferred embodiment, the shaker rotates the container with the container kept inclined.

In still another preferred embodiment, the apparatus further includes a controller for adjusting an inclination angle and a rotational speed of the container.

In yet another preferred embodiment, the container is detachably secured to the apparatus.

In still yet another preferred embodiment, the apparatus further includes a controller for adjusting a voltage to be applied to the shaker to control a degree of shaking the container by the shaker.

In a further preferred embodiment, the device for rotating or oscillating the container is a vibrating motor.

In a further preferred embodiment, the device for rotating or oscillating the container is a piezoelectric actuator.

The invention further provides an apparatus for arranging cells in a culture medium including a substrate having patterns on a surface thereof, the patterns each having different adhesive property to cells, a container containing therein the substrate, cells and liquid culture medium for incubating the cells, and a device for circulating the liquid culture medium in the container.

In a preferred embodiment, the device for circulating the liquid culture medium is a pump.

In another preferred embodiment, the apparatus further includes a controller for controlling a discharge of the pump to control a flowing speed of the liquid culture medium.

In still another preferred embodiment, a port of a feed pipe communicating the liquid culture medium to the pump, through which the liquid culture medium is absorbed into the pump from the container, is disposed at a location remote from the substrate or in the vicinity of a level of the liquid culture medium.

In yet another preferred embodiment, a port of a feed pipe communicating the liquid culture medium to the pump, through which the liquid culture medium is discharged into the container from the pump, is disposed at allocation remote from the substrate and near a level of the liquid culture medium.

In still yet another preferred embodiment, a feed pipe communicating the liquid culture medium to the pump, through which the liquid culture medium is discharged into the container from the pump, is provided with a branch pipe through which additional liquid culture medium is to be introduced into the container.

In a further preferred embodiment, a feed pipe communicating the liquid culture medium to the pump, through which the liquid culture medium is absorbed into the pump from the container, is provided with a branch pipe through which used liquid culture medium is discharged out of the apparatus.

In a further preferred embodiment, the patterns include a pattern on which collagen is applied and a pattern made of quartz.

In another aspect, the invention provides a method for incubating cells using a substrate having patterns on a surface thereof, the patterns each having different adhesive property to cells, the method including the step of shaking or circulating liquid culture medium in a container within all or a part of a period of time for incubating cells.

The advantages obtained by the aforementioned present invention will be described below.

As mentioned, the invention uses a substrate having patterns on a surface thereof, the patterns each having different adhesive property to cells, in order to arrange cells only on a desired pattern. During all or a part of the time for incubating cells, a culture medium is stirred by the device such as a shaker, a vibrating motor, a piezoelectric actuator and a pump. Hence, if cells are able to attach to a pattern processed make it difficult for cells to attach thereto, a flow of a culture medium prevents cells from attaching to such a pattern. It should be noted that a flow of a culture medium does scarcely prevent cells from attaching to a pattern which is processed so that cells easily to attach thereto, if a culture medium is not stirred too strongly. As a result, it is possible to attach cells to an area which is processed so that cells easily to attach thereto and to which cells are desired to attach, and not to attach cells to an area which is processed to make it difficult for cells to attach thereto and to which cells are not desired to attach, to thereby provide a higher resolution of cell arrangements. The invention makes it easy to apply cultivated cells to an artificial organ and a biosensor.

The above and other objects and advantageous features of the present invention will be made apparent from the following description made with reference to the accompanying drawings, in which like reference characters designate the same or similar parts throughout the drawings.

DESCRIPTION OF THE PREFERRED EMBODIMENTS

Preferred embodiments in accordance with the present invention will be explained below with reference to drawings.

EMBODIMENT 1

Figure 1A:
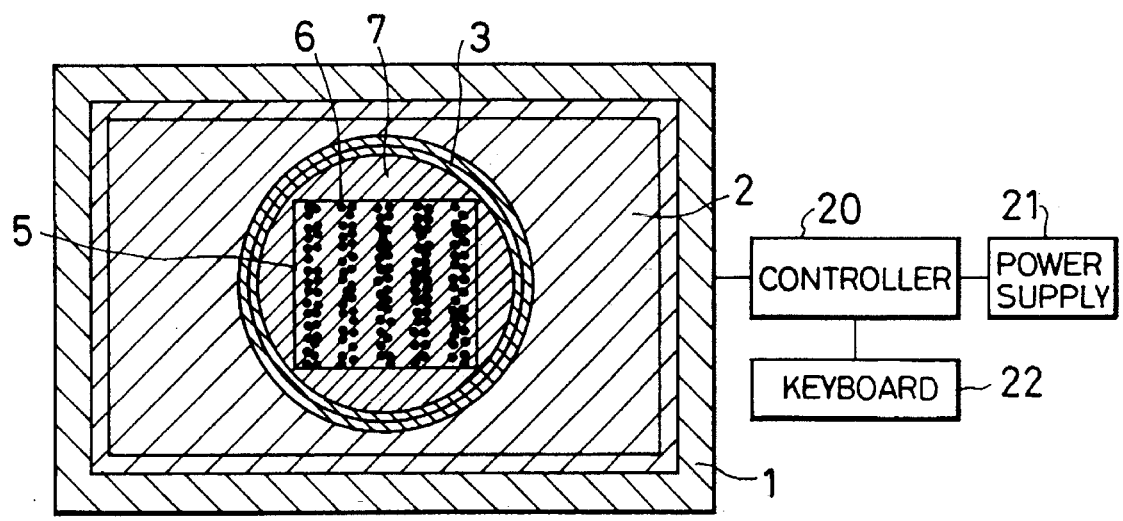
FIG. 1A is a cross-sectional view illustrating a first embodiment in accordance with the invention.
Figure 1B:
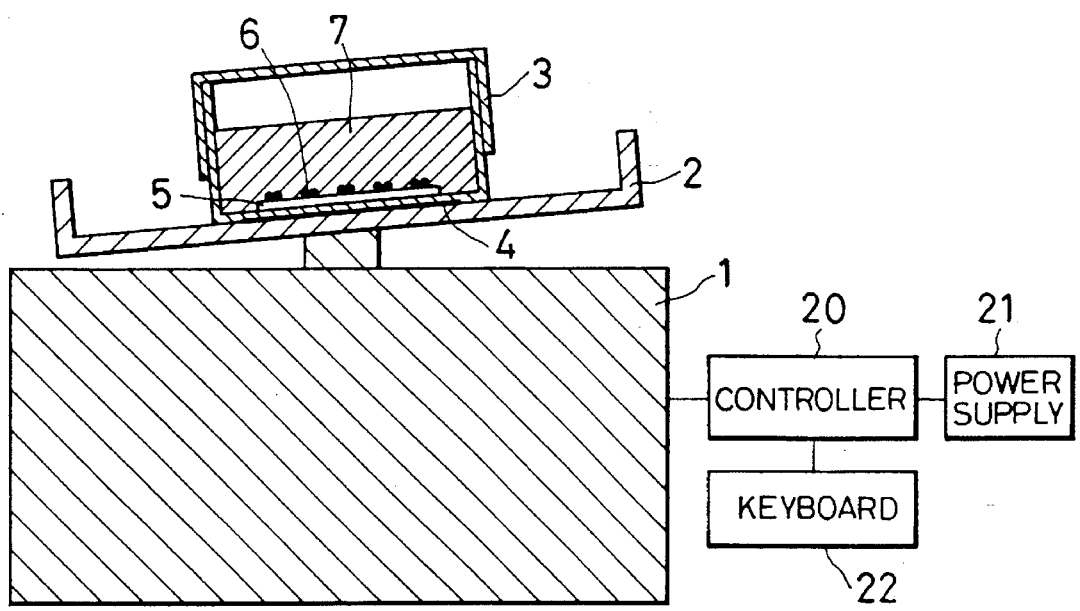
FIG. 1B is a longitudinal cross-sectional view of the first embodiment illustrated in FIG. 1A.

FIGS. 1A and 1B illustrate a first embodiment of an apparatus for arranging cells on a desired area of a substrate in accordance with the invention. The apparatus includes a shaker 1 having a table 2 on which a culture container 3 is fixed by two sided adhesive tape 4. The culture container 3 is made of polystyrene and has a diameter of 41 mm. The culture container 3 contains therein a substrate 5, cells 6 and liquid culture medium 7. The substrate 5 has a plurality of patterns formed on a surface thereof. Each of the patterns has different adhesive property to cells, more specifically, some patterns are processed so that cells easily to attach thereto, and others are processed to make it difficult for cells to attach thereto.

The table 2 can be inclined in the range of 0 to 10 degrees from a horizontal line and can also be kept in being inclined at a desired angle. In addition, the table 2 can be rotated at a speed in the range of 20 to 120 rpm. A controller 20 is electrically connected to a power supply 21 and also to the shaker 1 to control an inclination angle and a rotational speed of the table 2. A keyboard 22 may be electrically connected to the controller 20 so that an operator can manually input signals indicating a desired inclination angle and/or a desired rotational speed of the table 2. Since the table 2 is rotated while inclined, the culture medium 7 is stirred according to the rotational speed of the table 2. Stirring the culture medium 7 assures a higher resolution of cell arrangements.

The apparatus in accordance with the first embodiment makes it easy to control a degree of stirring the culture medium 7 to be an optimal degree for arranging cells on a desired area, by controlling the inclination angle and/or the rotational speed of the table 2 by means of the controller 20.

An adhesive strength of the adhesive tape 4 is determined so that the culture container 3 does not move on the table 2 or is not separated from the table 2 due to the shaking of the table 2. To make operation of the apparatus easy, it is preferable that the culture container 3 can easily be detached from the table 2. If such a condition is satisfied, other means for securing the culture container 3 to the table 2 may be chosen in place of the adhesive tape 4. For instance, the adhesive tape 4 may be replaced with a jig which can secure the culture container 3 through springs to the table 2.

EMBODIMENT 2

Figure 2A:
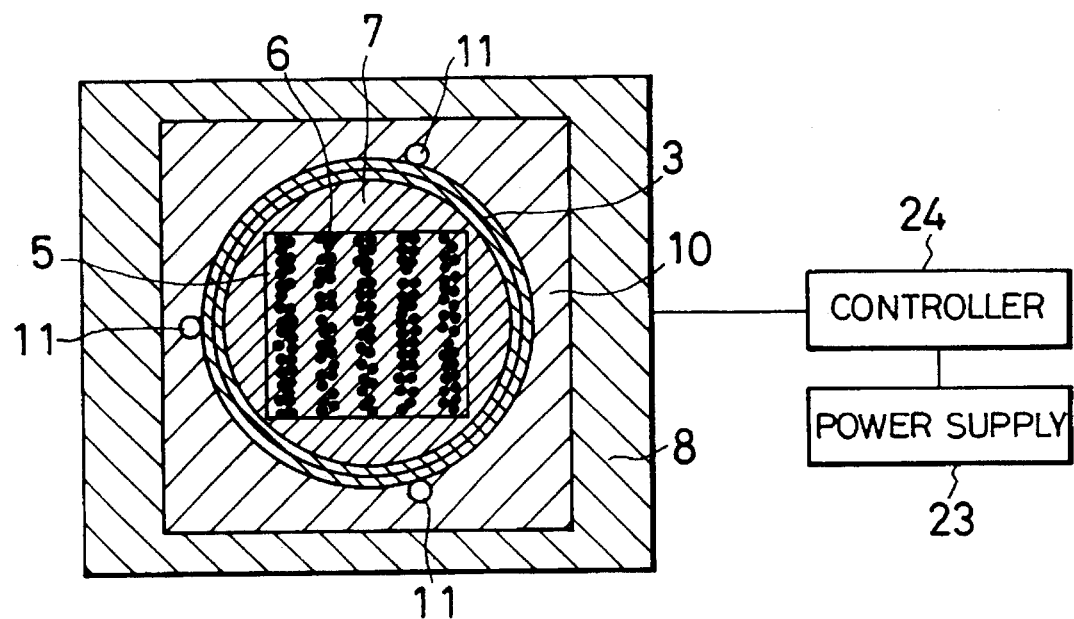
FIG. 2A is a cross-sectional view illustrating a second embodiment in accordance with the invention.
Figure 2B:
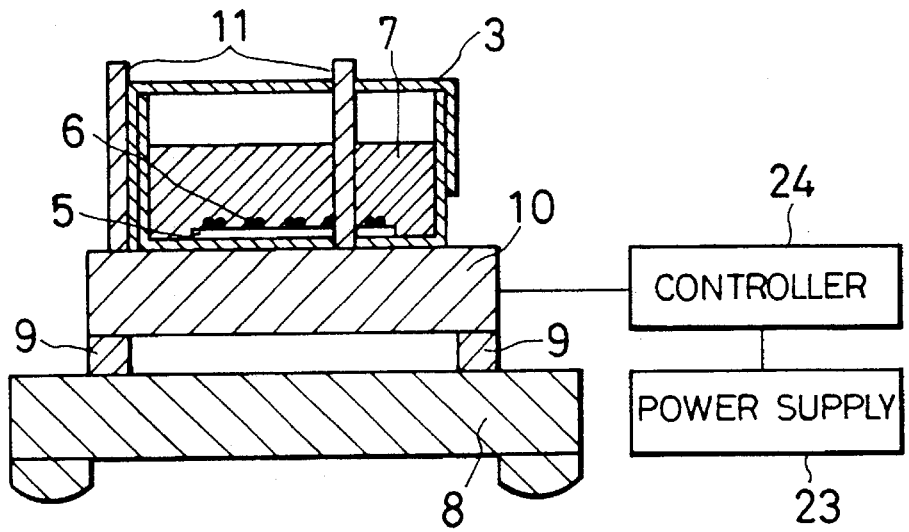
FIG. 2B is a longitudinal cross-sectional view of the second embodiment illustrated in FIG. 2A.

FIGS. 2A and 2B illustrate a second embodiment in accordance with the invention. An apparatus in accordance with the second embodiment has an oscillator 10 fixed on a base 8 through spacers 9. The oscillator 10 has three arms 11 which hold a culture container 3 so that the container 3 does not slide on the oscillator 10. In the embodiment, the oscillator is a micro vibrating motor, the type SE-7AL commercially available from Kabushikikaisha Shikoh Giken.

The culture container 3 contains therein a substrate 5, cells 6 and culture medium 7. The substrate 5 has a plurality of patterns formed on a surface thereof. Each of the patterns has different adhesive property to cells, more specifically, some patterns are processed so that cells easily to attach thereto, and others are processed to make it difficult for cells to attach thereto. The culture container 3 made of polystyrene and has a diameter of 41 mm.

The oscillation generated by driving the oscillator 10 is transferred to the culture container 3 through the arms 11 to thereby shake the liquid culture medium 7 contained in the culture container 3. Thus, a higher resolution of cell arrangements can be obtained.

The oscillator 10 is electrically connected to a power supply 2 through a controller 24 which varies a voltage to be applied to the oscillator 10 to thereby adjust a degree of shaking the culture container 3. A degree of shaking the culture container 3 may be s adjusted by providing spaces between the arms 11 and the container 3. The second embodiment has an advantage relative to the first embodiment in that an apparatus can be reduced in size.

Any device which can sufficiently oscillate the liquid culture medium 7 contained in the culture container 3 may be used as the oscillator 10. For instance, the vibrating motor comprising the oscillator 10 may be replaced with a piezoelectric actuator.

The arms 11 may be replaced with any other means for securing the container 3 to the oscillator 10 if the means can prevent the container 3 from moving on the oscillator 10 or from detaching from the oscillator 10. Similarly to the first embodiment, it is preferable that the culture container 3 can be easily detached from the oscillator 10 for making it easy to handle the apparatus.

If the oscillation of the oscillator 10 is transferred to the base 8, the entire apparatus is oscillated and hence it is impossible to stably install the apparatus. Accordingly, it is preferable that the spacers 9 are formed of a material, such as rubber which can absorb oscillation, in order to prevent the oscillation from transferring from the oscillator 10 to the base 8.

EMBODIMENT 3

Figure 3A:
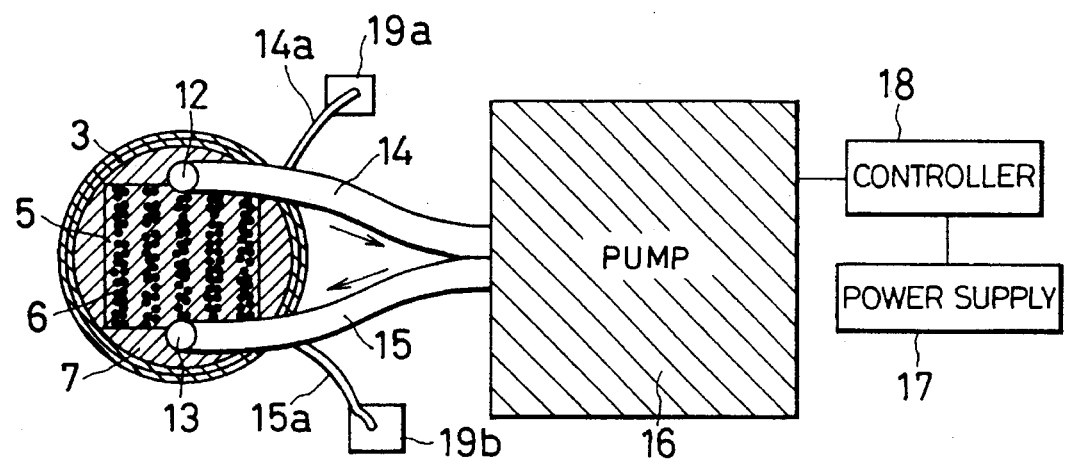
FIG. 3A is a cross-sectional view illustrating a third embodiment in accordance with the invention.
Figure 3B:
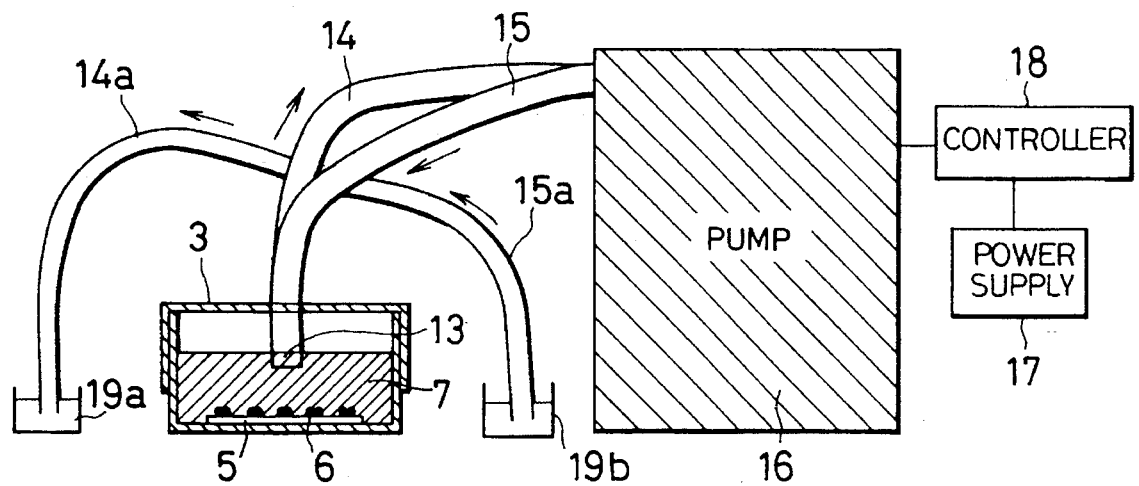
FIG. 3B is a longitudinal cross-sectional view of the third embodiment illustrated in FIG. 3A.

FIGS. 3A and 3B illustrate a third embodiment in accordance with the invention. A culture container 3 contains therein a substrate 5, cells 6 and liquid culture medium 7. The substrate 5 has patterns on a surface thereof, the patterns each having different adhesive property to cells, as in the first and second embodiments.

As illustrated in FIG. 3B, the liquid culture medium 7 is in fluid communication with a pump 16 through feed pipes 14 and 15, respectively. Both a port 12 of the feed pipe 14 and a port 13 of the feed pipe 15 are located near the level of the liquid culture medium 7 or immediately below the level of the liquid culture medium 7. The pump 16 is the micro tube pump MP-3 commercially available from Tokyo Rikakikai Kabushikikaisha. The culture container is made of polystyrene and has a diameter of 41 mm. The pump 16 circulates the liquid culture medium 7 contained in the culture container 3. That is, the liquid culture medium 7 is fed from the port 12 to the port 13 through the feed pipes 14 and 15 and the pump 16. Thus, the cells 6 are incubated with the liquid culture medium 7 flowing, and hence a higher resolution of cell arrangements can be obtained.

The pump 16 is electrically connected to a power supply 17 through a controller 18. The controller 18 varies a voltage to be applied to the pump 16 to thereby vary a discharge of the pump 16. Thus, a velocity of flow of the liquid culture medium 7 can be precisely controlled by the controller 18, to thereby provide a higher resolution of cell arrangements.

The port 12 of the feed pipe 14 may be disposed, for instance, at the side surface of the container 3 as well as immediately below a level of the liquid culture medium 7 as illustrated in Fig. 3B. It should be noted that it is not suitable to dispose the port 12 in the vicinity of the substrate 5. In the case of the embodiment, since the substrate 5 is located at the bottom of the culture container 3, it is not suitable to dispose the port 12 of the feed pipe 14 near the bottom surface of the container 3. The flow velocity of the liquid culture medium 7 is locally increased in the vicinity of the port 12 through which the medium 7 is absorbed by the pump 16. Thus, if the port 12 is located near the substrate 5, the cells 6 are prevented from attaching to an area of the substrate 5 located near the port 12. Accordingly, it is preferable to dispose the port 12 of the feed pipe 14 through which the liquid culture medium 7 is fed by the pump 16, at a location remote from the substrate 5 or a location near the surface of the liquid culture medium 7.

The port 13 of the feed pipe 15 through which the liquid culture medium 7 is introduced into the container 3 from the pump 16 may be disposed, for instance, at the side of the container as well as immediately below the level of the surface of medium 7 as illustrated in FIG. 3B. However, it is unsuitable to dispose the port 13 above a level of the liquid culture medium 7, because turbulent flow may be generated in the medium 7 due to impacts which would occur when the medium 7 fed through the pipe 15 is discharged into the medium 7 contained in the container 3. It is unsuitable to dispose the port 13 either in the vicinity of the substrate 5 or in the vicinity of the bottom surface of the container 3. The flow velocity of the liquid culture medium 7 is locally increased in the vicinity of the port 13 through which the medium 7 fed through the feed pipe 15 is discharged into the medium 7 contained in the container 3. Thus, if the port 13 is located near the substrate 5, the cells 6 are prevented from attaching to an area of the substrate 5 located near the port 13. Accordingly, it is preferable to dispose the port 13 of the feed pipe 15 at a location remote from the substrate 5 and, further, at a location not above a level of the medium 7, namely a location in the vicinity of a surface level of the liquid culture medium 7.

The feed pipe 14 may be formed with a branch pipe 14a communicating to a reservoir 19a, and the feed pipe 15 may be formed with a branch pipe 15a communicating with a reservoir 19b. Used liquid culture medium is discharged to the reservoir 19a through the branch pipe 14a, while new liquid culture medium is introduced to the medium 7 from the reservoir 19b through the branch pipe 15a. The provision of the branch pipes 14a and 15a makes it possible to automatically exchange old culture medium for new culture medium.

EMBODIMENT 4

Hereinbelow will be explained a method for arranging cells on a desired area of a substrate located in liquid culture medium. In the method, the apparatus in accordance with the first embodiment is used. The substrate 5 is a plate made of quartz having a thickness of 0.5 mm. On a surface of the substrate 5 is partially applied collagen to which cells tend to attach, and quartz, to which cells are unable to attach, is in exposure in other area than areas on which collagen is applied. An area on which collagen is applied is a circle having a diameter of 100 micrometers. A plurality of such circles are arranged on the substrate 5. A spacing between the adjacent circles is 100 micrometers. As the cells 6 are used unbilical vein endothelial cells "HUV-EC-4" derived from a human being commercially available from Dainipponseiyaku Kabushikikaisha, and as the liquid culture medium 7 is used a medium for human capillary blood vessel internal skin cells "CHL-MCDB 131" commercially available from Kurorera Kogyo Kabushikikaisha, to which are added 10% by weight of fetal calf serum and 10 ng/ml of fibroblast growth factor.

The table 2 of the shaker 1 was kept to be inclined at 5 degrees, and a rotational speed of the table 2 was set at 30 rpm. The culture container 3 containing the substrate 5 at the bottom surface thereof, the cells 6 and the liquid culture medium 7 was placed at the center of the table 2, and was fixed to the table 2 by means of the both-sided adhesive tape 4. Then, the apparatus was placed in an incubator in which a temperature is maintained at 37 degrees centigrade, $CO_2$ is contained by 5%, and humidity is saturated. The cells 6 were incubated for 24 hours with the table 2 being rotated every other ten minutes after five minutes had passed from the time at which the incubation started. As a result, it had been found that the greater number of the cells attached to the circles on which collagen was applied than the areas where quartz was in exposure. Thus, the cells were arranged only in desired areas.

While the present invention has been described in connection with certain preferred embodiments, it is to be understood that the subject matter encompassed by Way of the present invention is not to be limited to those specific embodiments. On the contrary, it is intended for the subject matter of the invention to include all alternatives, modifications and equivalents as can be included within the spirit and scope of the following claims.

What is claimed:

1. A method for arranging cells using a substrate having first and second patterns on a surface thereof, said first pattern being more adhesive for said cells than said second pattern, said method comprising the step of shaking or circulating liquid culture medium in a container within all or a part of a period of time for incubating cells, to attach said cells to said first pattern and prevent said cells from attaching to said second pattern.

2. The method in accordance with claim 1 wherein said patterns include a pattern on which collagen is applied and a pattern made of quartz.

\* \* \* \* \*